United States Patent [19]
Pawliszyn

[11] Patent Number: 6,042,787
[45] Date of Patent: Mar. 28, 2000

[54] DEVICE FOR SOLID PHASE MICROEXTRACTION AND DESORPTION

[76] Inventor: Janusz B. Pawliszyn, 383 Dunvegan Dr., Waterloo, Ontario, Canada, N2K 1W7

[21] Appl. No.: 08/818,038

[22] Filed: Mar. 14, 1997

Related U.S. Application Data

[63] Continuation-in-part of application No. 08/306,435, Sep. 19, 1994, Pat. No. 5,691,206, which is a continuation-in-part of application No. 07/934,736, Oct. 20, 1992, abandoned.

[30] Foreign Application Priority Data

Feb. 4, 1990 [GB] United Kingdom .................. 9007356
Feb. 4, 1991 [GB] United Kingdom .... PCT/CA91/00108

[51] Int. Cl.[7] ........................... G01N 30/04; G01N 30/16
[52] U.S. Cl. .............. 422/69; 422/88; 422/100; 73/23.41; 73/864; 73/864.81; 95/87; 95/89; 96/105
[58] Field of Search ................. 73/23.41, 61.55, 73/864, 864.01, 864.11, 864.21, 864.81; 95/89, 87; 96/105; 422/69, 70, 88, 89, 100

[56] References Cited

U.S. PATENT DOCUMENTS 5,700,695  12/1997  Yassinzadeh et al. .................. 436/180
5,744,095   4/1998  Smith ....................................... 422/58

*Primary Examiner*—Jan Ludlow
*Attorney, Agent, or Firm*—Daryl W. Schurr

[57] ABSTRACT

A device for carrying out solid phase microextraction is a tubular member having one closed end and one open end with an extracting surface within said tubular member. The extracting surface can be an extracting phase coating extending over a zone within the tubular member. The tubular member has a heater that can be used for either or both drawing fluid carrier into the tubular member or assisting in desorbing analytes into an injector of an analysis instrument. The tubular member can also be mounted in a housing with an airtight cavity and a plunger. A method of operation of the device is also provided. Previously, samples were analyzed using liquid-liquid extraction or using cartridges. Both of these methods are relatively expensive and time consuming. Both of these methods also require the use of solvents which can be difficult and expensive to dispose of.

35 Claims, 15 Drawing Sheets

DEVICE FOR SOLID PHASE MICROEXTRACTION AND DESORPTION

This is a continuation-in-part application of application Ser. No. 08/306,435 filed Sep. 19, 1994 now U.S. Pat. No. 5,691,206 which is a continuation-in-part application of application Ser. No. 07/934,736 filed Oct. 20, 1992 now abandoned.

BACKGROUND OF THE INVENTION

1. Field of the Invention

This invention relates to a method and device for solid phase microextraction and analysis and relates to microextraction and analysis being carried out using various types of a fiber, both solid and hollow, including a tubular member which can be made from various materials or coated with various materials or left uncoated.

2. Description of the Prior Art

Presently, in the organic analysis of environmental samples which involve the separation of components of interest from such matrices as soil, water, fly ash, tissue or other material, liquid extraction is traditionally used as the separation process. For example, water samples are usually extracted with organic solvent. Similarly, solid samples are leeched with an organic solvent in a SOXHLET apparatus. Methods based on solvent extraction are often time consuming, difficult to automate and are very expensive since they require high purity organic solvents and these organic solvents are expensive to dispose of. Further, the organic solids usually have high toxicity and are difficult to work with. In addition, the extraction processes can be highly non-selective. Therefore, sequential chromatographic techniques must sometimes be used to separate complex mixtures after extraction, significantly increasing the overall analysis time and the cost. EP-A1-159 230 discloses an extraction method of components in a liquid by placing packets of fibers in contact with said liquid in extracting the components.

Solid phase extraction is a known effective alternative to liquid-liquid extraction in the analysis aqueous samples. The primary advantage of solid phase extraction is the reduced consumption of high purity solvents and the resulting reduction in laboratory costs and the costs of solvent disposal. Solid phase extraction also reduces the time required to isolate the analyte of interest. However, solid phase extraction continues to use solvents and often suffers from high blank values. Further, there is considerable variation between the products offered by different manufacturers and lot-to-lot variation can be a problem when carrying out solid phase extraction procedures. Solid phase extraction cartridges available for manufacturers are normally constructed of plastic which can adsorb the analyte and increase interferences in the analysis. The disposable plastic cartridges used in the solid phase extraction process are first activated using organic solvent. The excess organic solvent is then removed and the sample to be tested is passed through the cartridge. The organic components from the sample are adsorbed on the chemically modified silica surface of the material in the cartridge. Both molecules of interest as well as interferences are retained on the cartridge material. During desorption, a selective solvent is chosen to first remove the interferences. The analyte is then washed out of the cartridge. The analytical procedure from that point is identical to that used in liquid-liquid extraction. The analyte is first preconcentrated and the mixture is then injected into an appropriate high resolution chromatographic instrument. Steps involving the use of organic solvents are the most time consuming.

SUMMARY OF THE INVENTION

A device for carrying out solid phase microextraction of components contained in a fluid carrier is characterized by, in combination, a fiber and a housing surrounding said fiber, said housing containing access means so that said carrier and components could be brought into contact with said fiber.

A method of carrying out solid phase microextraction and analysis with components contained in a carrier uses a fiber. The method is characterized by placing said fiber in contact with said carrier containing said components for a sufficient period of time for chemical extraction to occur, subsequently removing said fiber from said carrier and placing the fiber into a suitable analytical instrument and carrying out desorption with respect to at least one component on said fiber.

A method of carrying out solid phase microextraction and analysis with components contained in a carrier uses a fiber contained in a housing. The housing has access means so that said carrier can be brought into contact with said fiber. The method is characterized by contacting said fiber with said housing for a sufficient time to allow chemical extraction to occur, ending said contact and placing said fiber in a suitable analytical instrument in such a manner that desorption occurs with respect to at least one component on said fiber.

A device for carrying out solid phase microextraction of components contained in a fluid carrier has a tubular member having one closed end and one open end. There is a zone within said tubular member having an extracting surface. The tubular member has means to vary an interior temperature thereof with means to activate and deactivate said means to vary. The means to vary causes a pressure differential within said tubular member to draw a fluid carrier into said tubular member into contact with said extracting surface when said open end is in contact with said fluid carrier.

A device for carrying out solid phase microextraction of components contained in a fluid carrier has a tubular member having one closed end and one open end. The tubular member has an extracting surface therein. The tubular member has a heater to vary an interior temperature of said tubular member with means to activate and deactivate said heater. The open end of the tubular member permits contact between said fluid carrier and said extracting surface.

A method for carrying out solid phase microextraction of components contained in a fluid carrier using a tubular member having an open end and a closed end, a zone of said tubular member near said open end having an inner surface with an extracting phase coating thereon, said tubular member having a heater towards said closed end, with means for activating and deactivating said heater, said method comprising activating said heater to expand air within said member and expel some of said air through said open end, contacting said open end in said fluid carrier, subsequently deactivating said heater while maintaining said contact and drawing some fluid carrier into said tubular member in contact with said zone.

A method for carrying out solid phase microextraction of components contained in a fluid carrier using a tubular member having an open end and a closed end, a zone of said tubular member near said open end having an extracting surface located therein, said tubular member having a heater with means for activating and deactivating said heater, said method comprising carrying out microextraction with components of said fluid carrier, subsequently inserting said open end of said tubular member into an injector of an analysis instrument and activating said heater to expel analytes into said injector.

BRIEF DESCRIPTION OF THE DRAWINGS

FIG. 7b shows a chromatogram produced when using the prior art method of liquid-liquid extraction for the same components as those of FIG. 7a;

DESCRIPTION OF A PREFERRED EMBODIMENT

Figure 1:
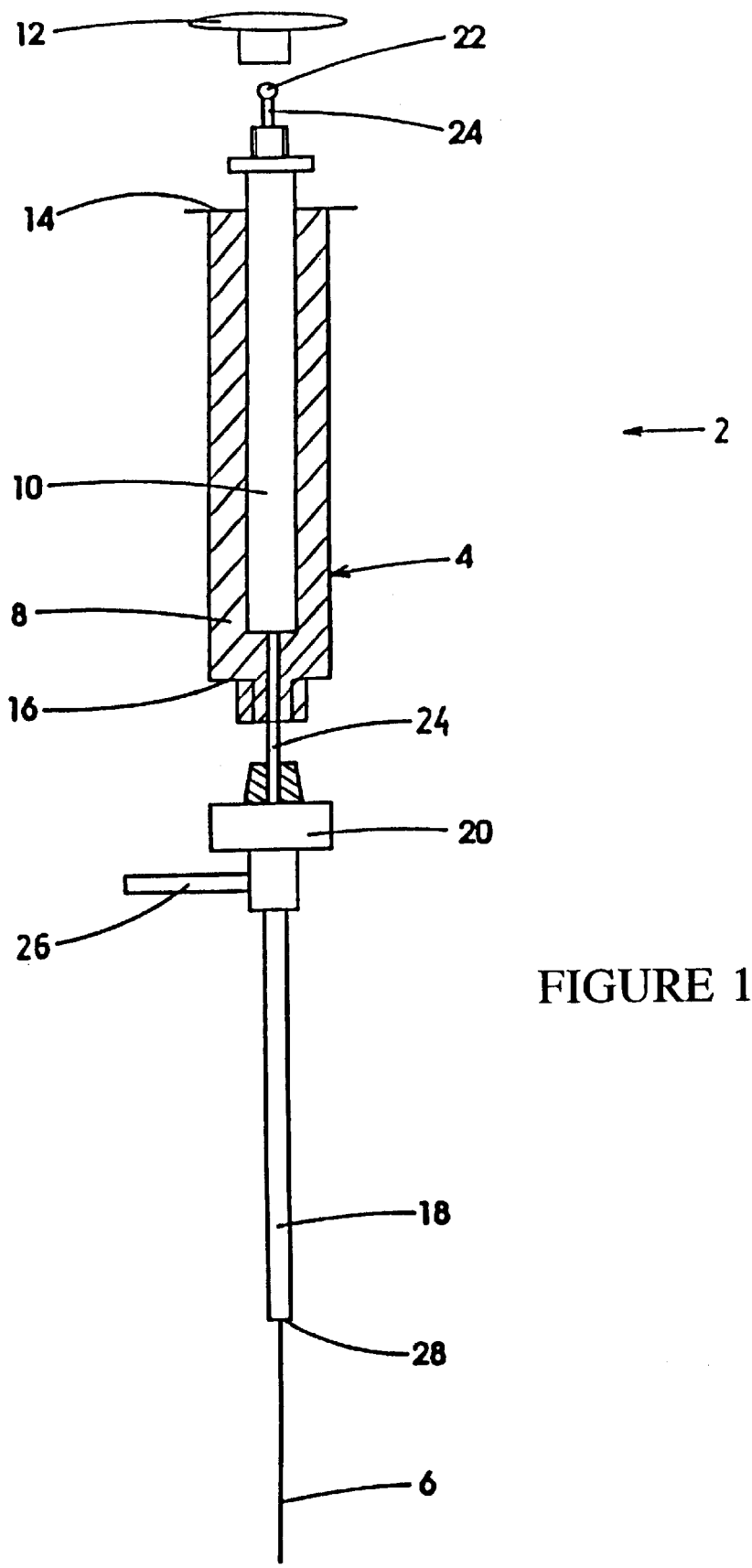
FIG. 1 is a partial sectional side view of a syringe and fiber with the plunger depressed.
Figure 2:
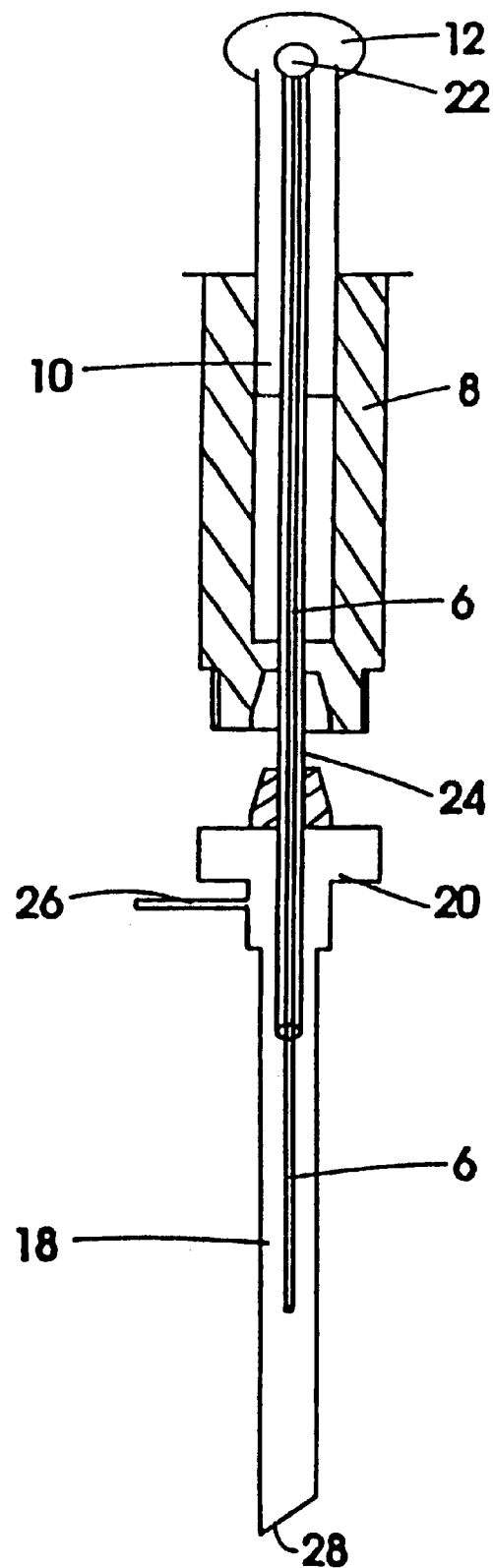
FIG. 2 is a schematic side view of a slightly different syringe and fiber with the plunger withdrawn.

Referring to FIGS. 1 and 2 in greater detail, a device 2 for carrying out solid phase microextraction has a syringe 4 containing a fiber 6. The syringe 4 is made up of a barrel 8 which contains a plunger 10 and is slidable within the barrel 8. The plunger 10 has a handle 12 extending from one end 14 of the barrel 8. At the opposite end 16 of the barrel 8, there is located a needle 18 which is connected to the end 16 by the connector 20. The handle 12 and the needle 18 and connector 20 are shown in an exploded position relative to the barrel 8 for ease of illustration.

The fiber 6 is a solid thread-like material that extends from the needle 18 through the barrel 8 and out the end 14. An end of the fiber 6 (not shown) located adjacent to the cap 12 has retention means 22 located thereon so that the fiber will move longitudinally as the plunger 10 slides within the barrel 8. The retention means can be simply a drop of epoxy which is placed on the end of the fiber 6 near the handle 8 and allowed to harden. The fiber 6 is partially enclosed in a metal sleeve 24 which surrounds that portion of the fiber 6 located within the plunger 10, the barrel 8 and part of the needle 18. The purpose of the metal sleeve 24 is to protect the fiber 6 from damage and to ensure a good seal during operation of the device. Extending from the connector 20 is an optional inlet 26. The purpose of the inlet 26 is to allow alternate access to the fiber. For example, when the fiber is contained within the needle 18, fluid could contact the fiber 6 by entering the inlet 26 and exiting from a free end 28 of the needle 18. The inlet 26 can also be used to contact the fiber with an activating solvent.

In FIG. 2, a schematic version of the device 2 is shown. The plunger is in a withdrawn position and the free end of the fiber 6 is located entirely within the needle 18. The access permitted by the inlet 26 when the fiber is in the position shown in FIG. 2 can readily be understood. Obviously, fluid contacting the fiber 6 within the needle 18 could also enter the free end 28 of the needle 18 and exit from the access 26.

Figure 3:
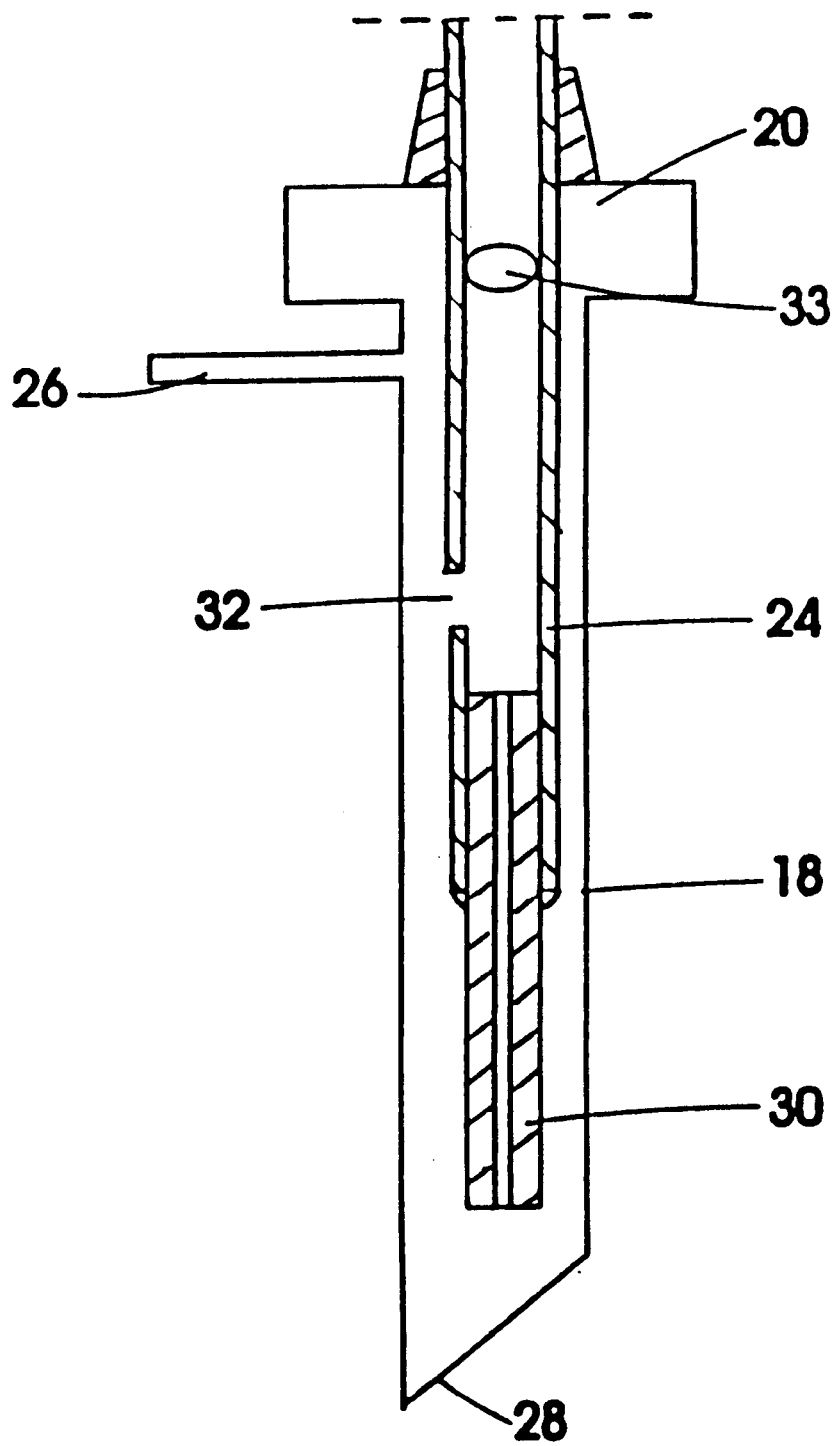
FIG. 3 is a schematic side view of a needle portion of a syringe containing a hollow fiber.

In FIG. 3, only the needle portion of the device is shown. A fiber 30 extending from the metal sleeve 24 is hollow. It can be seen that there is an opening 32 in the wall of the metal sleeve 24 to allow access to an interior of the sleeve 24 as well as an interior of the fiber 30. For example, fluid could enter the inlet 26 and an interior of the needle 18. Then, the fluid could pass through the opening 32 and through an interior of the fiber 30 and ultimately exit from the free end 28 of the needle 18. In this embodiment, the fiber does not extend to the handle 12 (not shown) but only the metal sleeve 24 extends to the handle 12. The fiber 30 can still be moved beyond the end 28 of the needle 18 by depressing the plunger and returned to the position shown in FIG. 3 by moving the plunger to the withdrawn position.

Alternatively, if it is desired to have the fiber 30 located within the needle 18 at all times, contact with the fiber 30 can be attained through the inlet 26 or the opening 32 and the free end 28. A plug 33 located within the metal sleeve 24 prevents any fluid from travelling up the sleeve to the handle. In some situations, the fluid could flow through the sleeve 24.

In general terms, the syringe could be said to be a housing for the fibers 6, 30 and the access means could be the action of the plunger 10 in moving the fiber beyond the end 28 or, alternatively, the access means could be the inlet 26.

The disadvantages and inconveniences of the previous processes for analyzing various fluids are overcome by the solid phase microextraction technique of the present invention. The diameter of the fibers will vary but will preferably be between 0.05 millimeters and 1 millimeter. Much of the experimentation on which the present invention was based, was carried out using fused silica fibers that were chemically modified. The fused silica fibers are widely used in optical communication and are often referred to as optical fibers.

Chemical modification of these fibers can be achieved by the preparation of the surface involving etching procedures to increase the surface area followed by chemical attachment of the desired coating. The stationary phases bonded to the surface of the silica fibers are similar to that used in fused silica gas chromatograph columns or high performance liquid chromatography columns.

As an example, fused silica fibers were obtained from Polymicro Technologies Inc., Phoenix, Ariz. and these fibers were coated with polyimide and had an outer diameter of approximately 171 µm. Uncoated fused silica was obtained by burning off the polyimide coating and gently scraping off the charred portion. To use the polyimide film as a stationary phase, it was first heated at 350° C. for four hours. The polyimide was then burned off and the char removed, except for a one to two millimeter portion at the end of the fiber. In all cases, the polyimide was burned off after the fiber had been inserted into the syringe and trimmed to the correct length. After burning, the fiber became fragile and had to be handled carefully. The metal casing is used to strengthen the fiber. The normal lifetime for a prepared fiber was five to six weeks with regular use.

The solid phase microextraction process does not require a sophisticated coating system to be a useful technique. Either the uncoated fiber, fused silica, silicone or the polyimide films that optical fibers are shipped with can be a suitable stationary phase.

The method of solid phase microextraction and analysis consists of a few simple steps. For example, when a water matrix sample containing components of interest is desired to be analyzed, the plunger of the syringe is depressed and the exposed fiber extending from the free end of the needle is inserted into the water matrix sample. The organic components of the water are extracted into the non-polar phase. Water is considered to be the carrier in a water matrix sample. Where the water sample is contained in a bottle containing a septum, the needle is inserted through the septum first before the plunger is depressed so that the fiber will not be damaged by the septum. When the microextraction has occurred to a sufficient degree (usually approximately two minutes), the plunger is moved to the withdrawn position causing the fiber to be drawn into the needle and the needle is removed from the sample bottle through the septum. Preferably, the sample is stirred while the fiber is inserted. The time for extraction will depend on many factors including the components being extracted as well as the thickness and type of coating, if any, on the fiber. Usually, the extraction time is approximately two minutes. The plunger is then moved to the withdrawn position to retract the fiber into the needle. The needle is then removed from the bottle and is inserted through the septum in an injection port of a conventional gas chromatograph or other suitable analytical instrument. The plunger is then depressed again to expose the fiber and the organic analytes on the fiber are thermally desorbed and analyzed. The fiber remains in the analytical instrument during the analysis. When the analysis has been completed, the plunger is moved to the withdrawn position and the syringe is removed from the injection port. Various injection ports are suitable such as the "split-splitless" type or the "on-column" type.

While various types of syringes will be suitable, a HAMILTON 7000 (a trade mark) series syringe has been found to be suitable. The syringe facilitates convenient operation of the solid phase microextraction process and protects the fiber from damage during the introduction into a sample bottle or into an injector of an analytical instrument or even during storage. The length of the fiber depends on the injector of the analytical instrument with which the fiber will be used. Preferably, the fiber is mounted in a housing to a movable part so that the fiber is movable longitudinally within the housing. Still more preferably, the movable part moves a sufficient distance so that at least part of said fiber can be extended outside of said housing and retracted into said housing successively. The movable part is preferably an elongated member which extends partially outside of the housing. The part of the elongated member that extends partially outside of the housing preferably has a handle thereon. The elongated member can be a plunger.

In addition to the improved convenience of the present device and method, the method differs significantly in the extraction part of the process compared to the prior art solid phase extraction process using cartridges. The extraction process in accordance with the present invention does not require prior sampling of aqueous material since in-vivo or in-vitro sampling can be conveniently performed. The microextractor can be directly inserted into the fluid stream. The simple geometry of the fiber eliminates clogging caused by particle matter present in the samples. Also, due to the small size of the fiber, not all of the organic compounds are extracted but rather the equilibrium described by the partition coefficient between the water and organic stationary phase for a given analyte is established. Therefore, the solid phase microextraction method of the present invention can be made selective by appropriate choice of a specifically designed organic phase. The partitioning between the aqueous phase and the organic coating can be described through the distribution constant, K:

$$K = \frac{C_s}{C_{aq}} \qquad (1)$$

where $C_s$ is the concentration in the stationary phase and $C_{aq}$ is the concentration in the water. The partition ratio, k', is therefore:

$$k' = \frac{C_s V_s}{C_{aq} V_{aq}} = \frac{n_s}{n_{aq}} = K \frac{V_s}{V_{aq}} \qquad (2)$$

where $n_s$ and $n_{aq}$ are the number of moles in the stationary and aqueous phases, respectively, and $V_s$ and $V_{aq}$ are the volumes of the respective phases. Rearranging Eqn. 2 yields:

$$ns = K \frac{V_s n_{aq}}{V_{aq}} \qquad (3)$$

substituting $C_{aq} V_{aq}$ for $n_{aq}$ results in:

$$n_s = K V_s C_{aq} = A C_{aq} \qquad (4)$$

where $A = KV_S$.

A linear relationship between concentration of analytes in aqueous samples and detector response is expected based upon the relationship in equation (4). The slope of the linearity curve can be used to determine the partition coefficient for a given analyte if the volume of the stationary phase is known. Furthermore, the sensitivity of the fiber can be adjusted by changing the volume (thickness or area) of the stationary phase.

The linear dynamic range of the method typically extends several orders of magnitude for coatings similar to chromatographic stationary phase materials. The limit of quantization depends on the partition coefficient and the thickness of the coating and can be as low as a few ppT (parts per trillion), which was obtained for chlorinated solvents. In this case the amount of the solvents extracted by a thick polyimide coating from a water sample is about 30 pg per component at a 1 μg/L concentration. This amount ensures not only ECD detection but will allow mass spectrometric identification and quantization.

Figure 4:
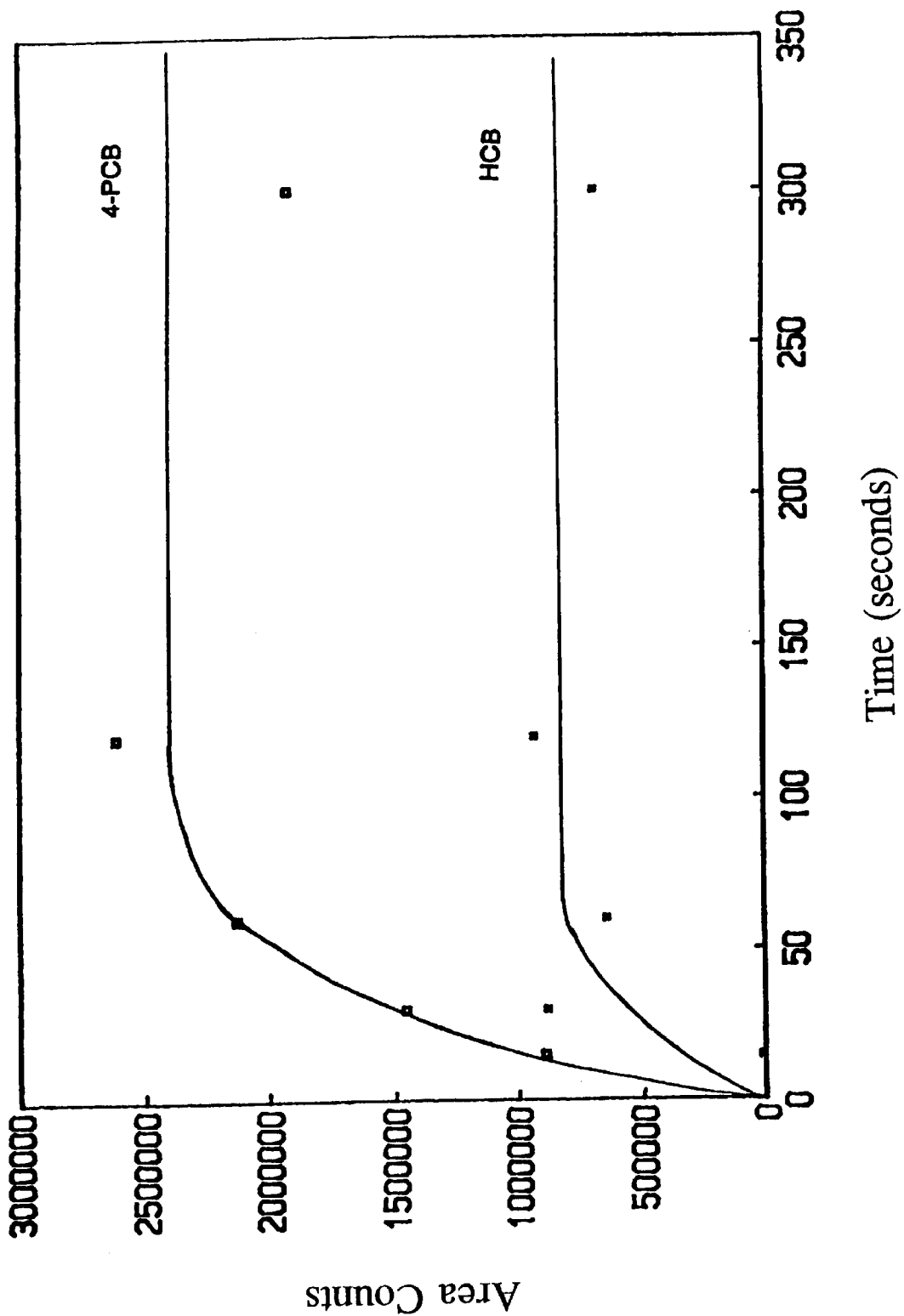
FIG. 4 is a graph of amount of analyte extracted versus time.

The dynamics of the extraction process is illustrated on FIG. 4 which shows an example of a typical relationship between the amount of analyte adsorbed onto the microextractor (peak area) versus the extraction time, which corresponds to the exposure time of the fiber to the water matrix sample. Initially, the amount of analyte adsorbed by the stationary phase increases with the increase in extraction time. This trend is continued until the point of steady state is achieved which causes the relationship to level off. This situation indicates the state of equilibrium between the concentration of the analyte in the stationary phase and in the water matrix sample and defines optimum extraction time. According to FIG. 3, optimum extraction time for uncoated fiber (about 0.1 μm film of silica gel) and PCBs as analytes is about one minute.

Figure 5:
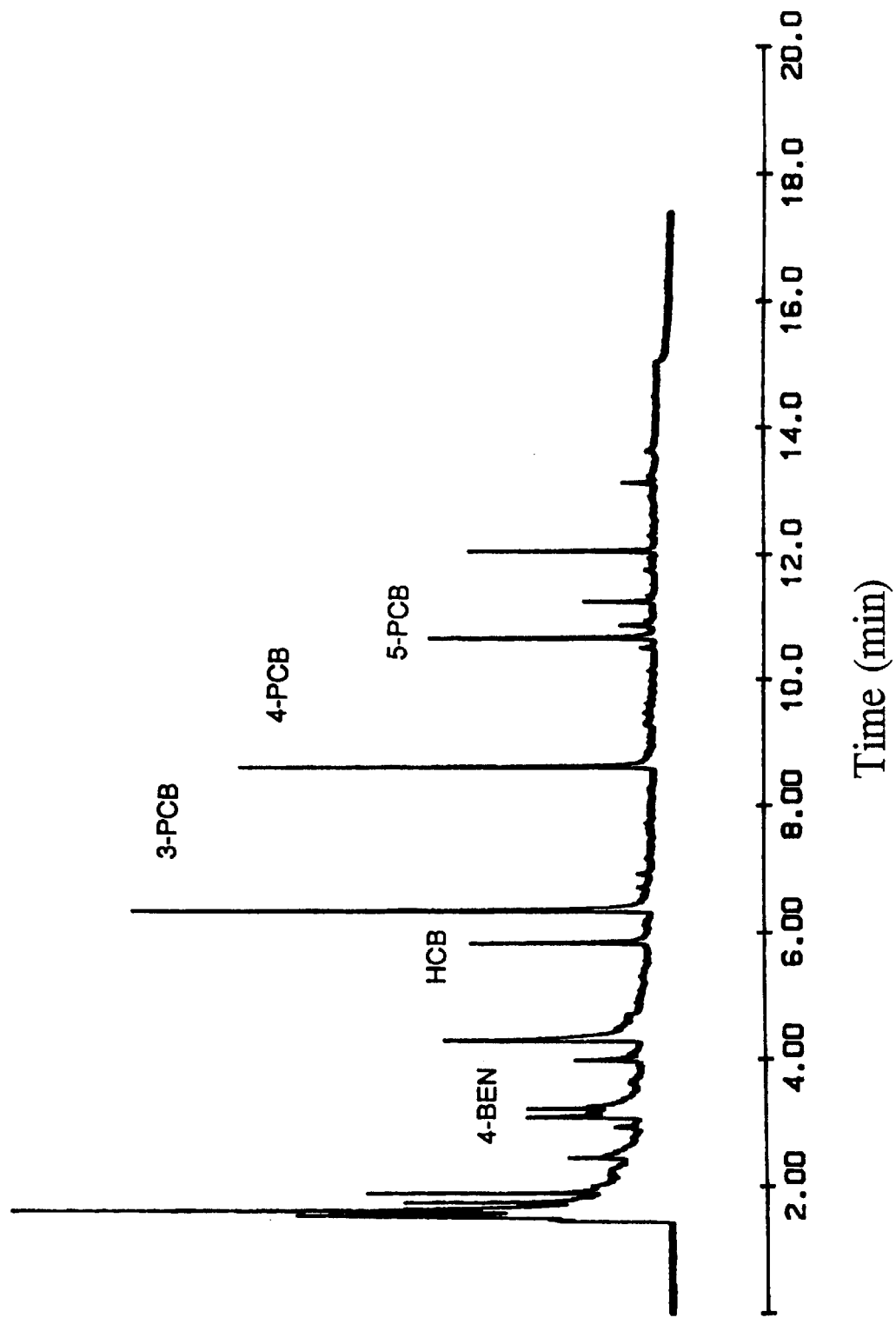
FIG. 5 is a graph showing the results of a typical gas chromatography analysis.

FIG. 5 illustrates the chromatogram corresponding to a PCB mixture in water extracted and analyzed by the solid phase microextraction method. Peak tailing is larger for the more volatile compounds than the heavier, later eluting components. This is an effect of thermal focussing that occurs when the analytes are volatilized at 300° C. and transferred to a 150° C. oven. The heavier compounds benefit from thermal focussing, but the oven is at too high a temperature to allow focussing of the more volatile compounds. The tailing can be alleviated by using a cryogenically cooled oven to improve focussing.

Figure 6:
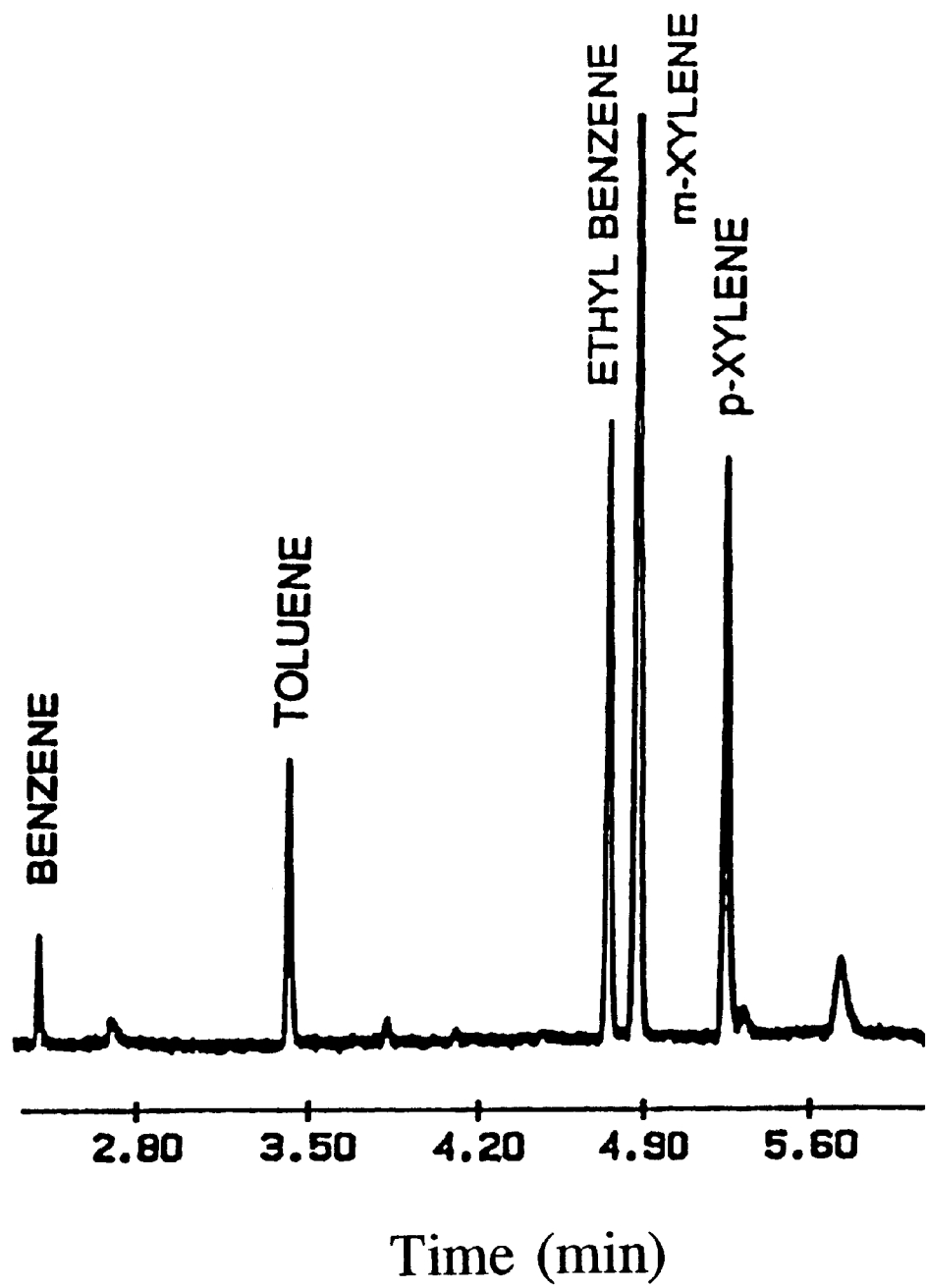
FIG. 6 is a graph showing another analysis from a gas chromatograph.

An uncoated fiber can also be used to adsorb benzene, toluene, ethyl benzene and xylenes (BTEX) from aqueous solutions. For this separation (FIG. 6), a flame ionization detector (FID) was used, illustrating that a sufficient quantity was adsorbed for FID detection. This expands the general applicability of the fiber as FID detectors are somewhat easier to operate and maintain than ECD detectors. The extraction efficiency in this case is sufficiently high to deplete significantly the analyte after 2 to 3 injections if a small volume of aqueous material (1 to 2 mL) is sampled. A larger sample volume (100 mL) is thus recommended if multiple injections are necessary.

Moderate levels of organic interferences and variation in ionic strength of aqueous solution do not significantly change the extraction equilibria. However, large amounts of organic solvent could be added intentionally to introduce partitioning selectivity, as is commonly done in liquid chromatography.

The fiber method has great potential for the analysis of highly sorptive compounds that can be difficult to sample without loss of analyte. Losses to storage bottles and transfer lines could potentially be eliminated by sampling in situ and analyzing the fiber in the field using portable gas chromatograph instrumentation. The device and method of the present invention can utilize a mechanical device such as an autosampler. The autosampler can be programmed to operate the plunger at the appropriate time to contact the carrier and to insert the syringe and the fiber into the injection port of the analytical instrument. The autosampler has an advantage over manual extraction and analysis in that the contact time and the length of the fiber in the carrier as well as in the instrument can be maintained constant. A VARIAN 3500 gas chromatograph and a VARIAN 8100 autosampler has been found to be suitable.

Possible applications of this technique include sampling of both surface and groundwater samples, either in situ or in the laboratory. It could potentially be used in on-line process applications or clinical analysis. Both of these applications benefit from the simplified sample preparation. The coating can be designed for either a broad scan of the organic contaminants (non-selective fiber coating) or selective sampling. This method, when combined with laser desorption, could reduce the sample extraction and analysis to a fraction of a minute. In this technique the optical fiber is used as a light guide. In a variation of the invention, the syringe could have a laser source affixed thereto with activation means and coupling optics to focus light onto the fiber which will transmit the light to a free end thereof to desorb the components thereon. Curie point heating and microwave desorption are alternative desorption methods. The fiber also shows promise as a method of studying the adsorption properties of polymers and for obtaining information about partitioning in liquid chromatographic systems.

Figure 7A:
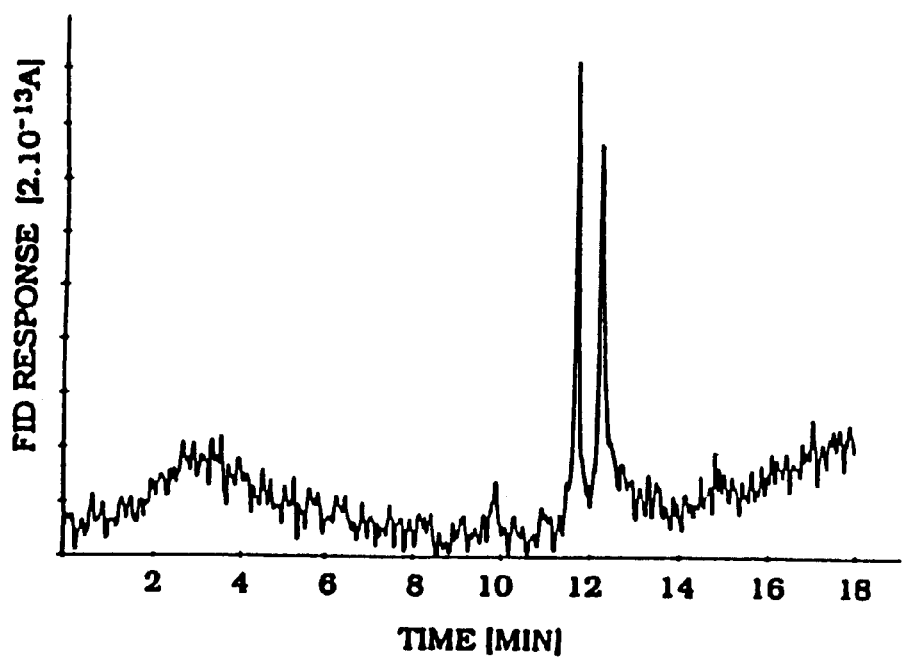
FIG. 7a shows a chromatogram produced when using the solid phase microextraction of the present invention.
Figure 7B:
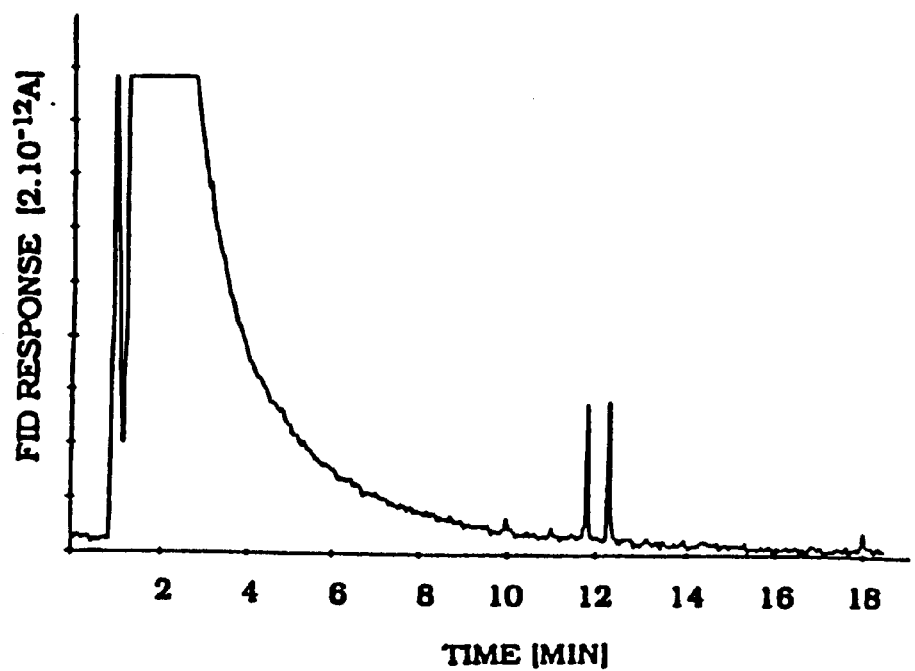

FIG. 7 illustrates the advantages of the method of the present invention compared to the prior art solvent procedure. The chromatogram from FIG. 7a corresponds to silica fiber techniques using C-18 coating and FIG. 7b to liquid-liquid extraction with chloroform. In both cases the same effluent from a sewage treatment plant was analyzed under the same chromatographic conditions. Results are similar, however the total extraction time was about an hour for the solvent method and two minutes for the fused silica fiber technique. The chromatogram for FIG. 7b shows the presence of the solvents used in the liquid-liquid extraction. The solid phase microextraction device facilitates easy sampling in the field. In addition, when organic solvents are used in the preparation step, the corresponding large peak together with possible impurities can mask volatile analytes (FIG. 7b).

Figure 8:
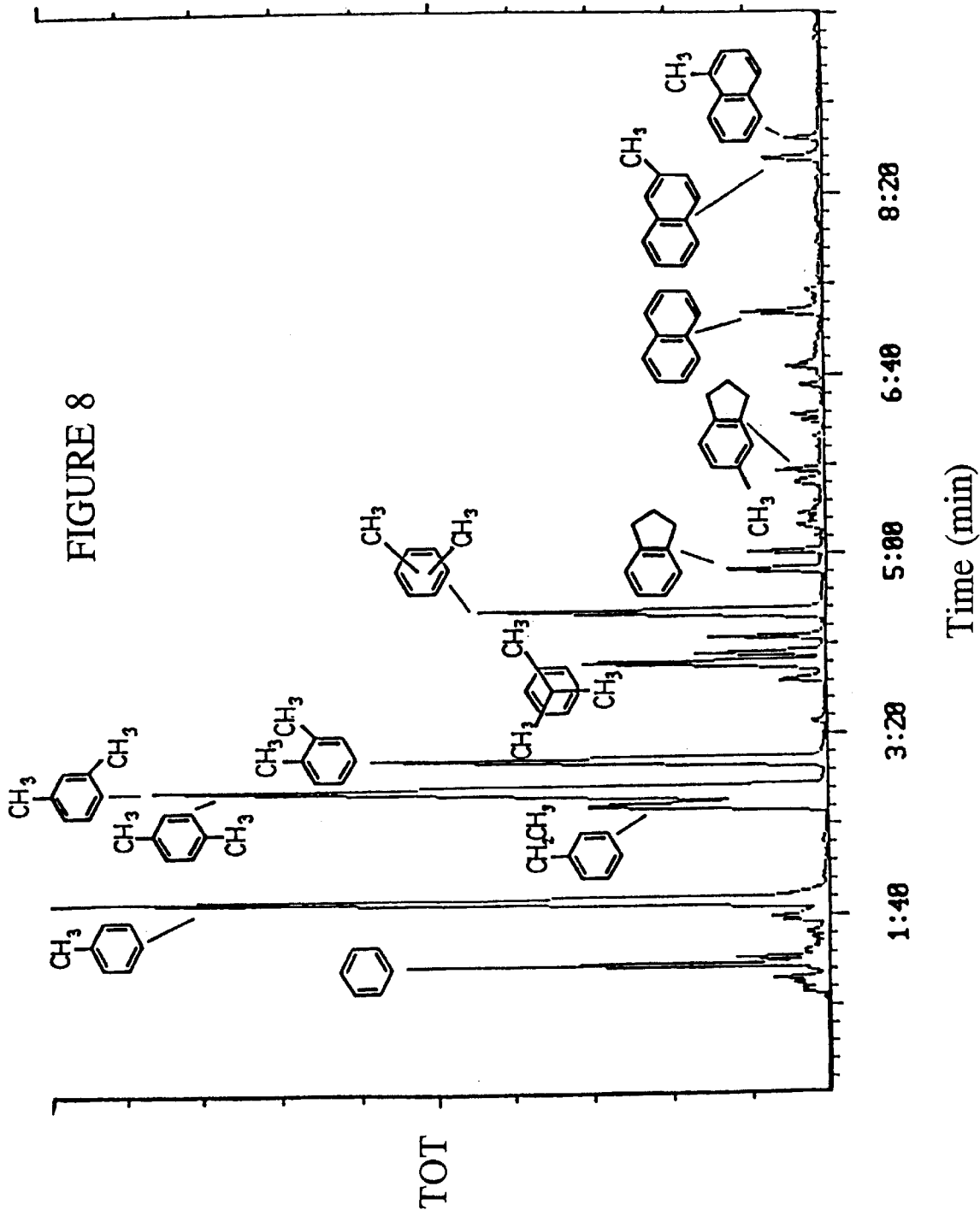
FIG. 8 is a chromatogram of the extraction of gasoline components from water with silicone coated fibers.
Figure 9:
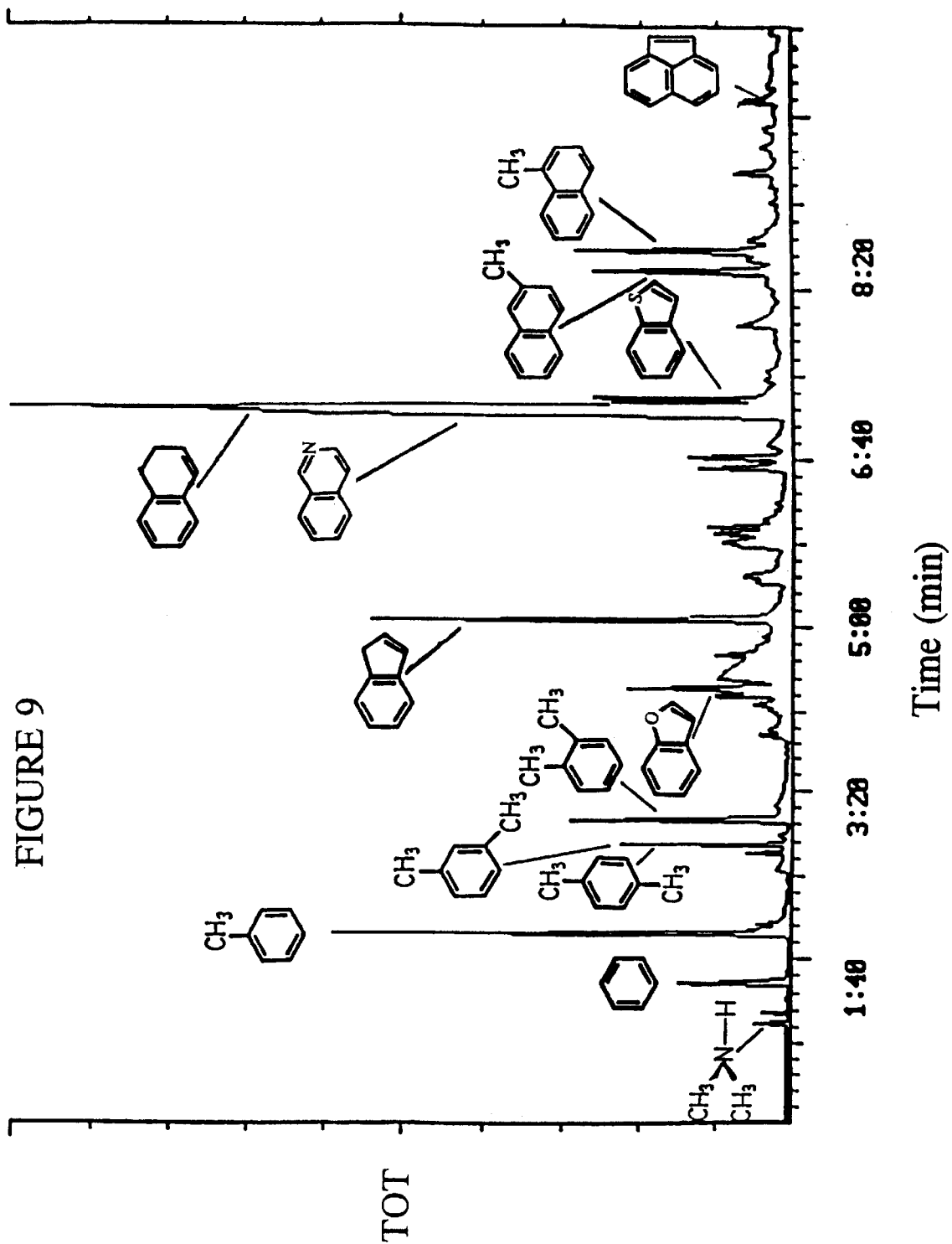
FIG. 9 is a chromatogram from the extraction of organics from coal gasification waste water using a silicone coated fiber.

In FIG. 8, there is shown a chromatograph for the extraction of gasoline components from water using a silicone coated fiber. In FIG. 9, there is shown a chromatograph for the extraction of organics from coal gasification waste water using a silicone coated fiber. Both analyses and identifications for FIGS. 8 and 9 have been done using a mass spectrometry detector.

Figure 10:
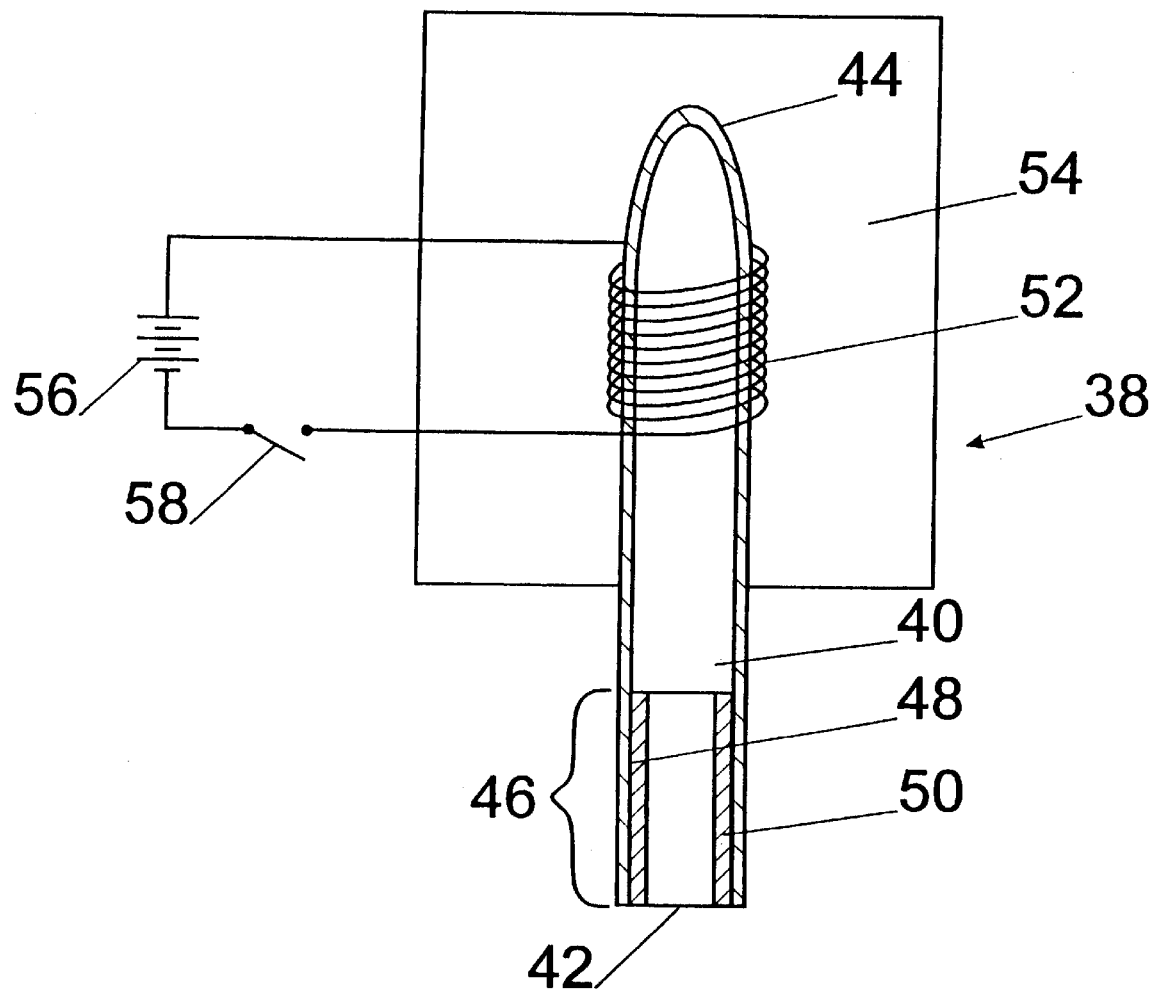
FIG. 10 is a schematic sectional side view of a tubular member having an extracting phase coating with a heater and cooler.

In FIG. 10, a device 38 for carrying out solid phase microextraction of components contained in a fluid carrier is shown. A tubular member 40 has an open end 42 and a closed end 44. Near the open end 42 is a zone 46 having an inner surface 48 with an extraction phase coating 50 thereon. The zone 46 could be located further into the tubular member 40 but is preferably located near the end 42. Also, the material from which the tubular member 40 is formed could be made of a material that would provide an interior extracting surface without the use of a coating. Near the closed end 44, there is located a heater 52 and a cooler 54 that are set up to heat and cool respectively the tubular member 40. The heater 52 is a coil connected to a power source 56 with switch means 58 to activate and deactivate the heater 52. The cooler 54 is preferably a Pelletier cooler and is connected in a conventional manner to a power source 59. Preferably, the tubular member 44 is a capillary having a circular cross-section. When reference is made to contact between a fluid carrier and the open end of the tubular member or the zone or extracting surface of the tubular member or similar variations thereof, the contact is intended to include and does include contact with a headspace of the fluid carrier.

In operation of the device 38, when it is desired to use the device, the heater 52 is activated by closing the switch 58, thereby heating up the tubular member 40 and causing air within the member to expand. Excess air exits through the open end 42. While the device is being heated, or immediately thereafter, the open end 42 is placed in contact with fluid carrier (not shown). Subsequently, the heater is turned off by opening the switch 58. Next, the cooler 54 is activated by activation means (not shown). Alternatively, the cooler can be activated while the heater is on so that the tubular member will cool more quickly when the heater is turned off. The cooler cools the air remaining within the tubular member and causes it to contract, thereby drawing carrier fluid into the open end 42 in contact with the extracting phase coating 50. When it is desired to analyze the carrier fluid within the tubular member 40, the open end 42 and that part of the tubular member near the open end 42 is inserted into an injector just as the cooler is deactivated. The injector desorbs analytes from the coating 50 into the analysis instrument. The heater is activated, once again, after the open end 42 has been inserted into the injector and after the cooler 54 has been deactivated. The activation of the heater 54 assists in expelling the analytes into the injector. The cooler 54 is optional. After the device has been heated to expel some of the air within the device, the heater is deactivated and, instead of using the cooler, the device can be left to cool as a result of the heater being deactivated. Further, while the heater is strongly preferred over the use of just a cooler, if the device were used without a heater but with a cooler, the cooler could be activated to draw fluid carrier into the tubular member when the open end is in contact with the fluid carrier. The cooler would remain activated until it was desired to desorb the analytes into an injector.

Figure 11:
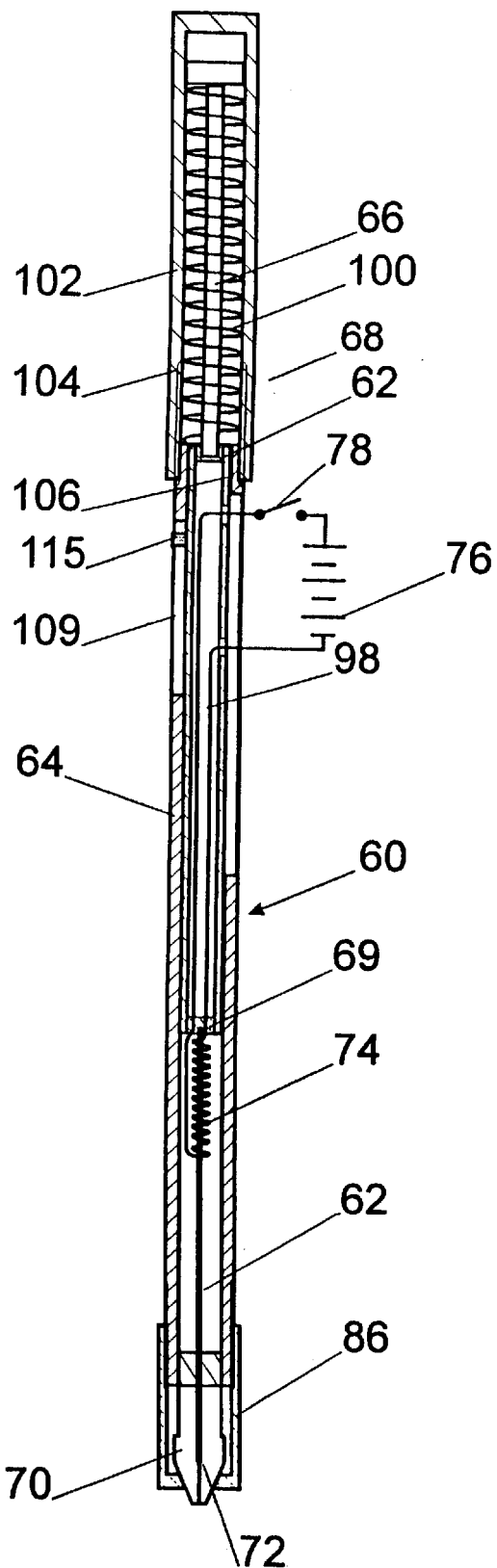
FIG. 11 is a sectional side view of a further embodiment of a tubular member contained within a housing with an airtight cavity located at an open end of said tubular member.
Figure 12:
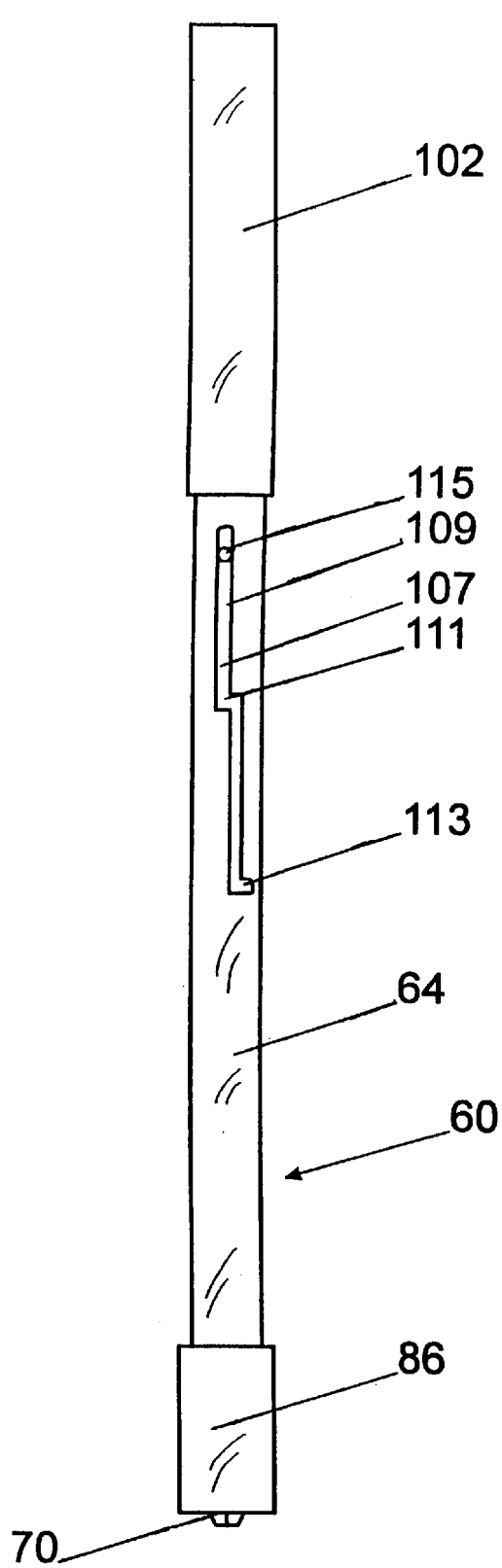
FIG. 12 is a side view of FIG. 11 showing a lock for a plunger.
Figure 13:
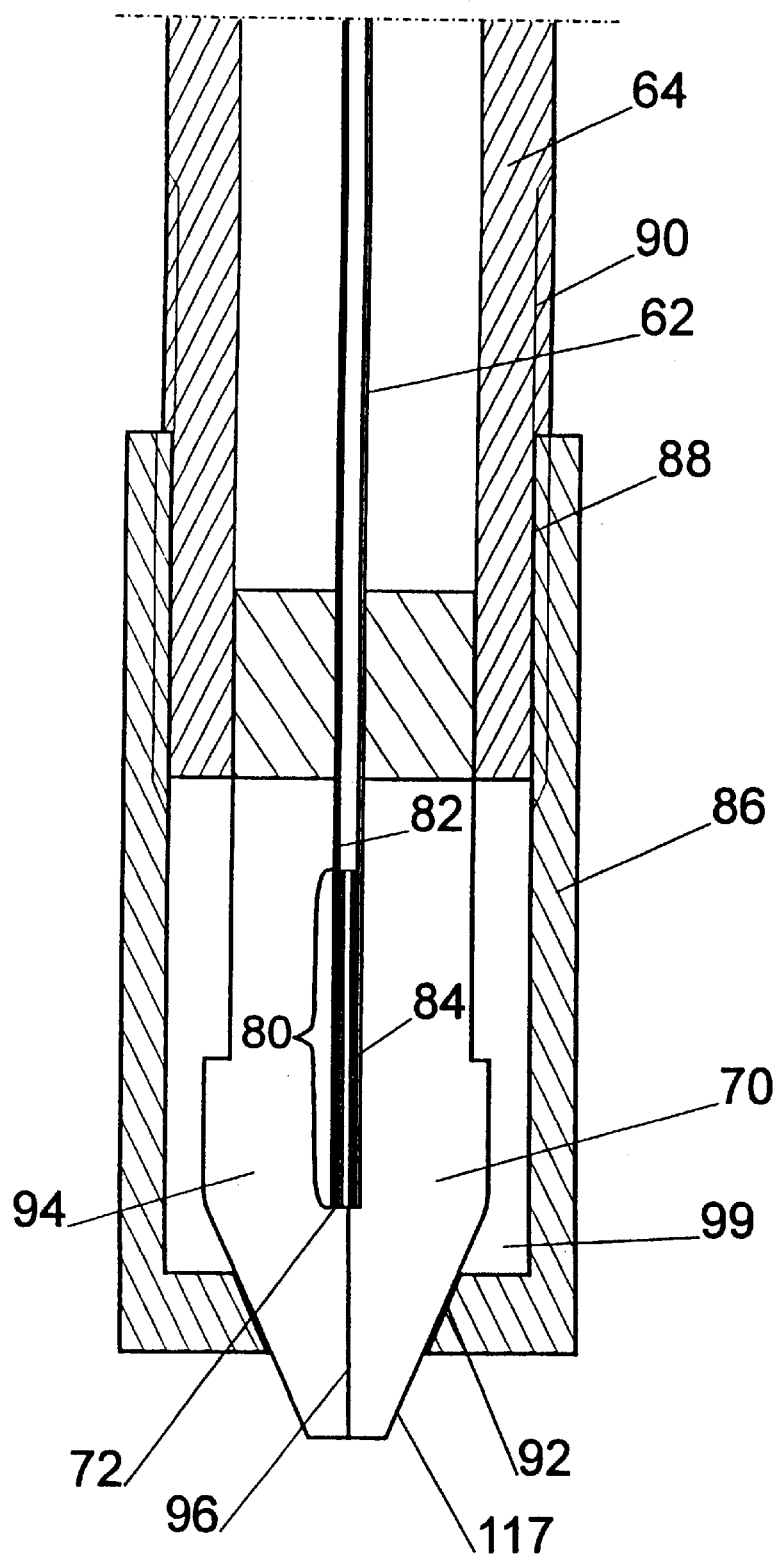
FIG. 13 is an enlarged view of said airtight cavity and said open end of said tubular member with said cavity in a closed position.

In FIGS. 11, 12 and 13, there is shown a device 60 for carrying out solid phase microextraction of components contained in a fluid carrier (not shown) A tubular member 62 is mounted within a housing 64. The tubular member has a plunger 66 located at a closed end 68 and an airtight cavity 70 located at an open end 72. The cavity 70 is shown in a closed position in FIGS. 11, 12 and 13. A heater 74 is located on the tubular member near the closed end 68. The heater 74 is connected to a power supply 76 and has switch means 78 to activate and deactivate said heater. Near the open end 72, there is located a zone 80 having an inner surface 82 with an extraction coating 84 located thereon. As with the device 38 of FIG. 10, the zone can be located further inside the tubular member from the open end 72, but is preferably located near the open end 72. Also, the tubular member could be a hollow fiber made of various materials, including metal. The material of the tubular member can be chosen so that the inner surface of the tubular member is an extracting surface without the use of a coating. An advantage of using coatings is the flexibility achieved to selectively extract various different components.

A cap 86 has a closed position and an open position (not shown in FIGS. 11 and 12). The cap 86 is mounted on the housing 64 by corresponding screw threads 88, 90 respectively that intermesh with one another. The cap can be designed to be completely removable from the housing 64 or to simply move to an open position. The cap has a centrally located opening 92 therein to assist in sealing the airtight cavity 70.

The cavity 70 is preferably comprised of four identical leaves 94 (only two of which are shown in FIGS. 11 and 13). In a closed position, the leaves are sealed along all area of contact 96. Preferably, the cavity 70 is made of soft metal and is still more preferably made of brass.

The plunger 66 is connected to the closed end 68 of the tubular member 62. The plunger is also connected to a slidable sleeve 98. When the plunger 66 is depressed (with the cavity 70 in the open position), the sleeve 98 and tubular member 62 slide longitudinally within the housing 64. The plunger is spring-mounted by a spring 100 that is biased to urge the plunger 66 to the retracted position shown in FIG. 11. In FIGS. 11 and 12, the plunger is actually shown in a slightly depressed position for ease of illustration. A removable closure 102 is screwed onto a top of the housing 64 by corresponding screw threads 104, 106 respectively. The purpose of the closure 102 is to prevent the plunger from being accidentally depressed. The sleeve 98 provides guidance for the tubular member 62 and also provides some protection for the tubular member. However, the sleeve 98 could be eliminated by making an appropriate change in an interior shape of the housing 64.

As can be seen from FIGS. 11 and 12, the device 60 has a lock 107 thereon. The lock 107 has a vertical channel 109 located in the housing 64 with a middle horizontal section 111 and a lower horizontal section 113. A protrusion 115 extends from the sleeve 98. Before the plunger is depressed, the cavity 70, which is shown in a closed position in FIGS. 11 and 12, must be moved to the open position. When the plunger is depressed, the protrusion 115 reaches the middle horizontal section 111, the plunger can be twisted or rotated slightly counterclockwise relative to the housing 64 to lock the plunger in the middle stage position. When it is desired to depress the plunger further, the plunger can be manually depressed until the protrusion 115 reaches the lower horizontal section 113. The plunger and sleeve can then be twisted or rotated still further in a counterclockwise direction to lock the plunger into a lower stage position.

When it is desired to release the plunger from either the lower stage or the middle stage position, the plunger can be turned slightly in a clockwise direction. This will allow the protrusion and the plunger to move upward.

Figure 14:
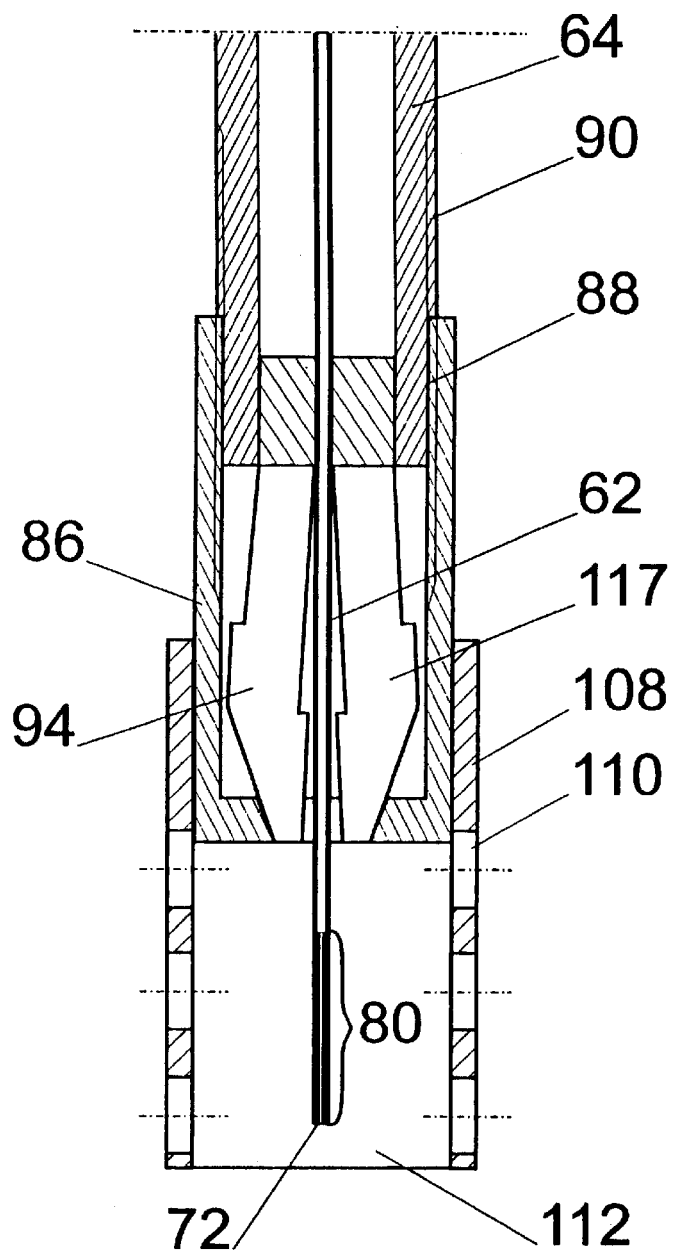
FIG. 14 is a partial sectional side view of the device of FIG. 11 with the cavity in an open position and a plunger depressed.

In a further embodiment shown in FIG. 14, the cap 86 has a shield 108 mounted thereon. The shield protects the cavity 70 and the tubular member 62 from damage when the tubular member extends beyond the cavity 70. The shield contains various perforations 110 and a main opening 112 to allow access of the fluid carrier (not shown). It can be seen that the leaves 94 of the cavity 70 are in an open position in FIG. 14 and the plunger has been depressed to the middle stage as the open end 72 of the tubular member 62 extends beyond the cavity 70 into an area of the shield 108 where the open end can be placed in contact with carrier fluid (not shown). In order for the cavity 70 to open, the cap 86 must be moved from the closed position shown in FIGS. 11, 12 and 13 to the open position shown in FIG. 14. In order to move the cap from the closed position to the open position, the cap must be loosened slightly by twisting it counterclockwise when viewed from the bottom relative to the housing 64. The cap does not have to be completely removed from the housing 64 as long as it is opened a sufficient distance that the leaves 94 spread apart from one another as shown. The leaves 94 are preferably biased to spring outward when the pressure from the cap 86 at the opening 92 is released. Thus, as the cap is loosened, the opening 92 moves downward vis-a-vis the cavity 70 from the position shown in FIG. 13 to the position shown in FIG. 14. The leaves 94 then spread apart. In order to close the cavity 70, the cap 86 is turned clockwise, when viewed from the bottom, vis-a-vis the housing 64 and the opening slides up a tapered edge 117 of the cavity 70 to the position shown in FIG. 13. As the cap is turned onto the housing, the leaves 94 will close gradually until they are completely closed when the cap has been tightened onto the housing 64. Of course, the plunger must be released and unlocked to retract the tubular member to the position shown in FIG. 13 before beginning to close the cavity 70.

Figure 15:
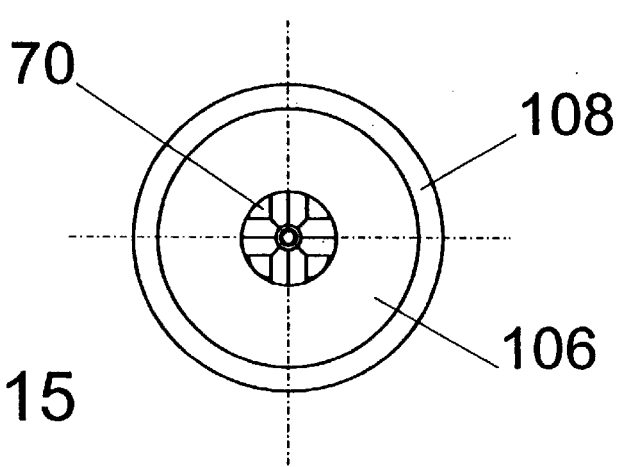
FIG. 15 is an end view of the device shown in FIG. 14.

An end view of the device shown in FIG. 14 is set out in FIG. 15. It can be seen that the shape of the shield 108 and cap 86 is cylindrical and that the cavity 70 has a circular cross-section.

Figure 16:
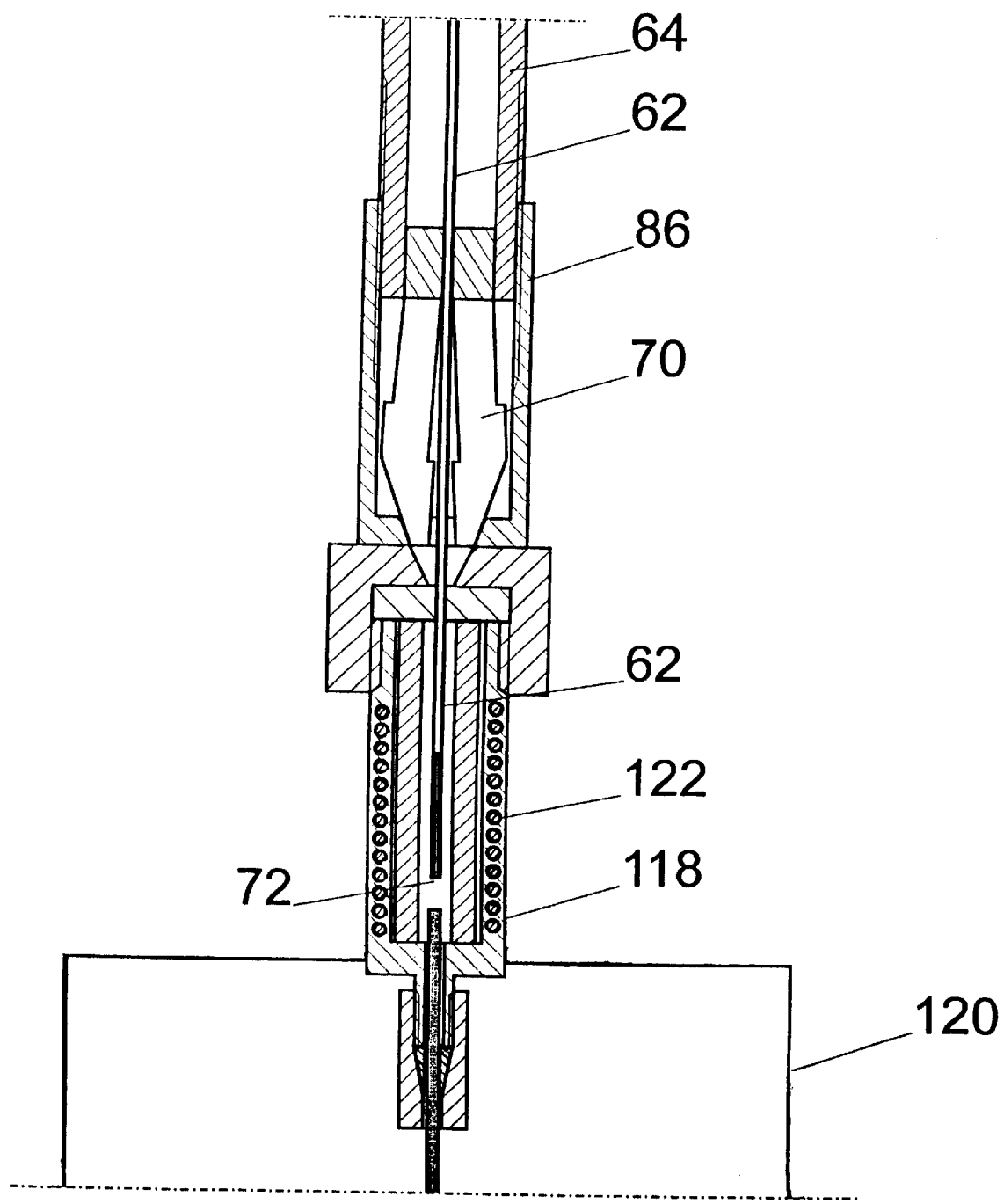
FIG. 16 is a schematic partial sectional side view of the device of FIG. 11 aligned with an injector of an analysis instrument.

As shown in FIG. 16, when the tubular member 62 contains a fluid carrier (not shown) and it is desired to analyze one or more components of that fluid carrier, the cavity 70 can be reopened by loosening the cap 86 with respect to the housing 64. The plunger can then be depressed to the lower stage so that the tubular member enters an injector 118 of an analysis instrument 120. The injector 118 has heating means 122 thereon to desorb analytes from the fluid carrier and the coating into the analysis instrument 120. The heater 74 (not shown in FIG. 16) is activated to further assist in expelling analytes into the analysis instrument 120. It should be noted that the shield 108 has been removed in FIG. 16 to bring the cavity 70 closer to the injector 118. If desired, the device 60 could be designed so that the tubular member is long enough and the plunger can be depressed far enough so that the tubular member can be made to enter the injector without removing the shield 108.

The lock 107 is optional as is the spring 100 for the plunger. Without the spring, the plunger will remain in whatever position it is placed in and the lock is not necessary. Even if the plunger is spring-mounted, the lock is still not necessary as the plunger can be held in a depressed position for the desired time period when the tubular member is exposed beyond the cavity 70.

In operation of the device 60, starting from the closed position of the cavity 70 as shown in FIG. 12, the closure 102 is removed to expose the plunger 66 and the cap 86 is loosened to open the cavity 70. The heater 74 is then activated by closing the switch 78 to heat the air within the tubular member and expel some of the air through the open end 72. Preferably, while the heater is still activated, or just after the heater is deactivated, the plunger is depressed and the open end is placed in contact with a fluid carrier (not shown). Preferably, the plunger is rotated relative to the housing to lock the plunger in a middle stage position with the tubular member extending beyond the cavity. The heater is then deactivated, causing the air within the tubular member to contract. As the air contracts, some of the fluid carrier is drawn into the open end 72 into contact with the coating 84 in the zone 80. The plunger is then released and will return to the retracted position. Then, the cap 86 is tightened to close the cavity 70 and the closure 102 is replaced over the plunger 66.

With either the device 38 or the device 60, it is not necessary to activate the heater when using the device to contact air in order to draw the air into the tubular member to contact the extracting surface. The heater can be left in a deactivated mode during microextraction and used only during desorption when the tubular member is inserted into an injector. For example, in-tube solid phase microextraction can be carried out using either the device 38 or the device 60. The device 60 is preferred because the contact between the zone of the tubular member and the fluid carrier can be limited or restricted by not moving the tubular member outside of the cavity after the cavity has been opened. Also, the amount that the cavity 70 is opened can be adjusted by loosening the cap 86 to a point between the open and closed position. For example, the present invention can be used for in-tube solid phase microextraction sampling.

The device 60 can then be transported to a location having a suitable analysis instrument. The closure 102 is removed and the cap 86 is loosened to open the cavity 70. The device 60 is aligned with the injector. The plunger is then depressed to the middle stage and then twisted vis-a-vis the housing and immediately moved to the lowermost stage. At this stage, the plunger is twisted again in a counterclockwise direction when viewed from the top of the plunger to lock the plunger in position in the lowermost stage. In this position, the tubular member extends into the injector 118 as shown in FIG. 16.

The injector heating means 122 is then activated as is the heater 74 of the device 60. When the analytes have been desorbed into the injector, the heater 74 is deactivated, the plunger is released from the lowermost stage and twisted to ultimately return the plunger back to the retracted position shown in FIG. 11. The cap 86 is then retightened to close the cavity 70 and the closure 102 is replaced over the plunger. An advantage of using the heater 74 during desorption is that the tubular member is "cleansed" and is ready for reuse for carrying out solid phase microextraction again with respect to the same or different components.

Figure 17:
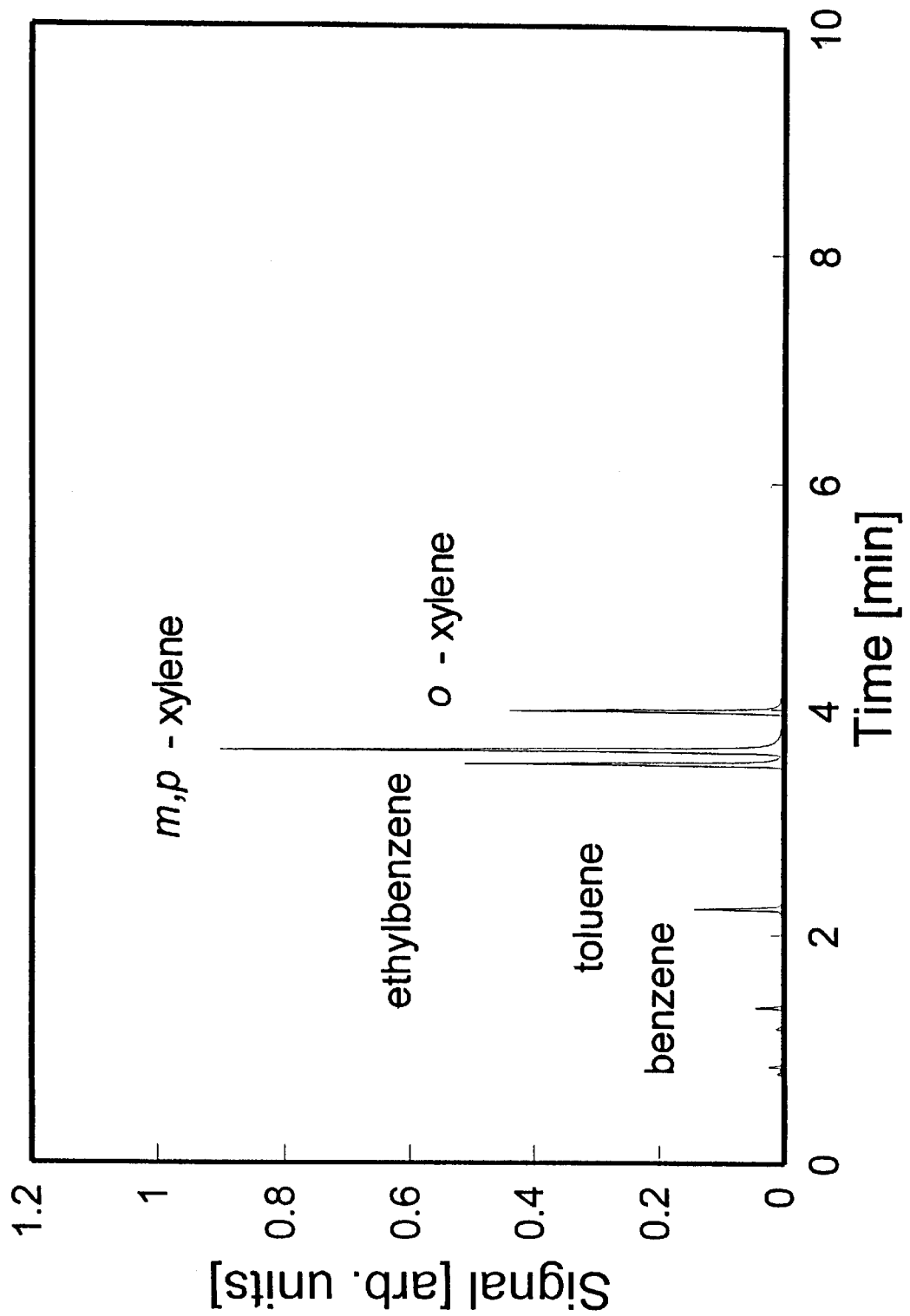
FIG. 17 is a graph showing the results obtained with the device of FIG. 10.

In FIG. 17, the peaks representing the components are shown when the heater is used to assist the heat source of the injector in desorbing analytes into the injector. The peaks are sharper when the heater 74 is used during desorption and are more rounded when the heater is not used.

In addition to the analyte concentration measurement at a well defined place in space and time, obtained by using the approaches discussed above, an integrating sampling is possible with a simple SPME system. This is particularly important in field measurements when changes of analyte concentration over time, and place to place variations, must often be taken into account.

When the extracting phase is not exposed directly to the sample, but is contained in the tubular member or needle without any flow of the sample through it (as discussed above), the extraction occurs through the static gas phase present in the tubular member. The integrating system can consist of an extracting phase coating on the interior of the tubing as shown in FIGS. 3, 10 or 11, or it can be an externally coated fiber withdrawn into the needle as shown in FIGS. 1 and 2. These geometric arrangements represent a very powerful method able to generate a response proportional to the integral of the analyte concentration over time and space (when the tubing or needle is moved through the space). In these cases, the only mechanism of analyte transport to the extracting phase is diffusion through the gaseous phase contained in the tubing. During this process, a linear concentration profile is established in the tubing between the small needle opening, characterized by surface area A and the position of the extracting phase, located at the distance Z from the opening. The amount of analyte extracted, dn, during time interval, dt, can be calculated by considering the first Fick's law of diffusion:

$$dn = AD_g \frac{dc}{dz} dt = AD_g \frac{\Delta C(t)}{Z} dt \qquad (5)$$

where $\Delta C(t)/Z$ is a value of the gradient established in the needle between needle opening and the position of the extracting phase, Z; $\Delta C(t)=C(t)-C_z$, where $C(t)$ is a time dependent concentration of analyte in the sample in the vicinity of the needle opening, and $C_z$ concentration of the analyte in the gas phase in the vicinity of the coating. $C_z$ is close to zero for a high coating/gas distribution constant capacity, then: $\Delta C(t)=C(t)$. The concentration of analyte at the coating position in the needle, $C_z$, will increase with integration time, but it will be kept low compared to the sample concentration in the sample $C(t)$ because of the presence of the sorbing coating. Therefore the accumulated amount over time can be calculated as:

$$n = D_g \frac{A}{Z} \int C(t) dt \qquad (6)$$

As expected, the extracted amount of analyte is proportional to the integral of a sample concentration over time, the diffusion coefficient of analytes in gaseous phase, $D_g$, area of the needle opening, A, and inversely proportional to the distance of the coating position in respect of the needle opening, Z. It should be emphasized that equation 5 is valid only in a situation where the amount of analyte extracted onto the sorbent is a small fraction (below RSD of the measurement, typically 5%) of equilibrium amount in respect to the lowest concentration in the sample. To extend integration times, the coating can be placed deeper into the needle (larger Z), the opening of the needle can be reduced by placing an additional orifice (smaller A), or a high capacity sorbent can be used. The first two solutions will result in a low measurement sensitivity. An increase of sorbent capacity presents a more attractive opportunity. It can be achieved by either increasing the volume of the coating, or its affinity towards the analyte. An increase of the coating volume will require an increase of the device size. The optimum approach to increased integration time, is to use sorbents characterized by large coating/gas distribution constants.

While air will be the usual atmosphere within the tubular member, obviously, other atmospheres can be utilized in the same manner as described with respect to air. In some embodiments, it may be preferable to coat a fiber which can be made of metal or other material and to fixedly insert the fiber inside the tubular member so that the coating on the fiber provides the extracting surface rather than an interior surface of the tubular member itself or a coating on the interior surface of the tubular member itself. Also, when a cooler is used with the device along with a heater, it is preferable to turn the heater on either before or just after the heater is activated and to leave the cooler on so that the extracting surface cools more quickly once the heater is deactivated. While a battery is preferably mounted on the device 60 to operate the heater so that the device is completely self-sufficient, the device 60 could be designed with connectors for connecting the heater to an external power source or the device 60 could be designed to operate both from a battery mounted on the device and/or from an external power source where, for example, the battery is dead.

The device and method of the present invention can also be used for extraction and analysis of gases and for supercritical fluids as well. The method is not limited to analysis of organic analytes but also for inorganic ions by using ion-exchange materials located on the fiber surface. In addition to thermal desorption by direct heating, laser desorption or conductive heating, for example, microwave desorption or Curie point magnetic hysteresis method could be used. Both solid fibers and hollow fibers, or other tubular members, will be suitable depending on the use that is being made of the present invention. For example, fused silica, graphite fibers, fibers constructed with solid polymeric materials and even metal and metal wires can be used as fibers and the fibers can be coated with various materials or uncoated. Some suggested coatings are CARBOWAX (a trade mark), poly(dimethylciloxane), poly(divilylbenzene), poly(divinyldibenzene), carbon, NAFION (a trade mark), nylon, octadecyltrichlorosilane, polymethylvinylchlorosilane, liquid crystalline polyacrylates, silicone, polyimide, grafted self-assembled monolayers and inorganic coatings. Fibers coated with these coatings are stored under nitrogen or helium to prevent absorption of the volatile organics present in air. The coatings can be organic or inorganic, for example, fused silica surface.

In addition to having coating located on an outer surface of a solid fiber, coating could be located on an inner surface of a hollow fiber or other tubular member. Coating could also be located on the packing material used with the fiber.

In addition to direct extraction, the method of the present application could be performed with prior activation using organic solvents by using the optional inlet 26 on the syringe. The analytical instrument used with the method of the present invention can also be varied. For example, a gas chromatograph, a liquid chromatograph or a supercritical fluid chromatograph could be used. Other analytical methods such as flow injection analysis, mass spectrometry, atomic absorption or emission including inductively coupled plasma technique could be used.

In addition to analyzing for environmental contaminants, the method and device of the present invention can be used to monitor or measure the components in industrial process streams. The present invention can also be used to study properties of coatings, for example, absorption, deterioration rates and diffusion coefficients.

Numerous other variations, within the scope of the attached claims, will be readily apparent to those skilled in the art.

I claim:

1. A device for carrying out solid phase microextraction of components contained in a fluid carrier, said device comprising;

(a) a tubular member having one closed end and one open end, a zone within said tubular member having an extracting surface;

(b) said tubular member having means to vary an interior temperature thereof, with means to activate and deactivate said means to vary, said means to vary causing a pressure differential within said tubular member to draw a fluid carrier into said tubular member into contact with said extracting surface when said open end is in contact with said fluid carrier ;

(c) said tubular member being located within a housing, said housing having an airtight cavity at said open end of said tubular member, said cavity having a movable wall, said wall providing an open position and a closed position for said cavity said cavity sealing said open end when in said closed position and permitting contact between said fluid carrier and said open end when in said open position, said movable wall always being connected to said cavity.

2. A device as claimed in claim 1 wherein an extracting surface of said zone is formed by an extracting phase coating on a surface of said tubular member within said zone.

3. A device as claimed in claim 2 wherein said zone extends along a length of said tubular member.

4. A device as claimed in claim 3 wherein said means to vary an interior temperature is a heater connected to a power source, said heater being activated to expand air within said tubular member thereby creating a positive pressure differential to expel air within said tubular member, said heater being deactivated when said open end of said tubular member is in contact with said fluid carrier, the deactivation of said heater creating a negative pressure differential within said tubular member to draw said fluid carrier into contact with said zone.

5. A device as claimed in claim 4 wherein said zone is located near said open end.

6. A device as claimed in claim 4 wherein the tubular member has a cooler with means to activate and deactivate said cooler, said cooler being activated to draw further fluid carrier into contact with said zone when said heater is deactivated with said open end in contact with said fluid carrier.

7. A device as claimed in claim 4 wherein said heater is powered by a power source selected from a group of a battery and a transformer connected to an AC power source.

8. A device as claimed in any one of claims 2, 4 or 5 wherein said coating is formed of a material selected from the group of non-polar and polar coatings.

9. A device as clued in any one of claims 2, 4 or 5 wherein the coatings are formed of a material selected from the group of poly(dimethylciloxane), poly(divinyldibenzene), poly (divinyldibenzene), carbon, monomers with minor amounts of ionomers produced by copolymerization of fluorocarbon appropriate acid or ester, nylon, polyethylene glycol, silicone, polyimide, octadecyltrichlorosilane, polymethylvinylchlorosilane, liquid crystalline polyacrylates, grafted self-assembled monolayers and inorganic coatings.

10. A device as claimed in any one of claims 1, 4 or 5 wherein the tubular member is a capillary.

11. A device as claimed in any one of claims 1, 4 or 5 wherein said tubular member is a hollow fiber.

12. A device as claimed in claim 1 wherein said cavity has at least two parts that seal against one another along a line of contact when said cavity is in said closed position and separate from one another when said cavity is in said open position, said parts always being connected to said cavity.

13. A device as claimed in claim 12 wherein said tubular member has a heater with means to activate and deactivate said heater.

14. A device as claimed in any one of claims 12 wherein said zone is located near said open end.

15. A device as claimed in claim 14 wherein said tubular member is a hollow fiber.

16. A device as claimed in claim 1 wherein said cavity has four parts that seal against one another along lines of contact when said cavity is in said closed position and separate from one another when said cavity is in said open position, said parts always being connected to said cavity.

17. A device as claimed in claim 12 wherein said closed end of said tubular member is connected to a plunger, said tubular member being slidable within said housing, said plunger being depressed when said cavity is in said open position, to expose said tubular member outside of said cavity, said plunger being retracted before said cavity is moved to said closed position.

18. A device as claimed in claim 17 wherein said housing has a cap mounted thereon at an end of said housing where said cavity is located, said cap having an open position and a closed position, said cavity being in a closed position when said cap is in a closed position, said cavity being in an open position when said cap is in an open position, said cap having a centrally located opening to receive said cavity and to assist in sealing said cavity when said cavity is in a closed position.

19. A device as claimed in claim 18 wherein said cap is connected to said housing by way of corresponding screw threads, said cap having a perforated shield extending outward therefrom to protect said tubular member when said tubular member extends beyond said cavity.

20. A device as claimed in claim 17 wherein said plunger is spring-mounted whereby a spring urges said plunger to return to the retracted position.

21. A device as claimed in claim 20 wherein said plunger has locking means for releasably locking said plunger in a depressed position.

22. A device as claimed in any one of claims 17, 18 or 19 wherein said housing has a removable closure located to cover said plunger when said plunger is not in use.

23. A device as claimed in any one of claims 17, 18 or 19 wherein said means to vary said temperature is a heater for said tubular member, said heater being connected to a power source located on said device, said heater being connected so that said heater will be activated for a finite time period when said plunger is depressed, said heater automatically deactivating after said time period has expired even though said plunger remains in a depressed position.

24. A device as claimed in any one of claims 12, 16 or 17 wherein said means to vary said temperature is a heater for said tubular member with means to activate and deactivate said heater, said heater being powered by a power source and being activated to expel air from within said tubular member, said heater being deactivated when said tubular member is in contact with said fluid carrier, the deactivation of said heater creating a negative pressure differential within said tubular member to draw said fluid carrier into contact with said zone.

25. A device as claimed in any one of claims 1, 12 or 16 wherein said cavity is made from a soft metal.

26. A device as claimed in any one of claims 1, 12 or 16 wherein said cavity is made from brass.

27. A device as claimed in any one of claims 1, 3 or 12 wherein said means to vary is a heater for said tubular member, said heater being located between said zone and said closed end.

28. A device for carrying out solid phase microextraction of components contained in a fluid carrier, said device comprising:

(a) a tubular member having one closed end and one open end, said tubular member having an extracting surface therein;

(b) said tubular member having a heater to vary an interior temperature of said tubular member with means to activate and deactivate said heater;

(c) said open end of said tubular member permitting contact between said fluid carrier and said extracting surface;

(d) said tubular member being located within a housing, said housing having an airtight cavity at said open end of said tubular member, said cavity having a movable wall, said wall providing an open position and a closed position for said cavity, said cavity sealing said open end when in said closed position and permitting contact between said fluid carrier and said open end when in said open position, said movable wall always being connected to said cavity.

29. A device as claimed in claim 28 wherein said extracting surface extends along a zone of said tubular member.

30. A device as claimed in claim 29 wherein said extracting surface is a surface of said tubular member.

31. A device as claimed in claim 29 wherein said extracting surface is an extracting phase coating on a surface of said tubular member.

32. A device as claimed in claim 31 wherein said closed end of said tubular member is connected to a sleeve and a plunger is connected to said sleeve, said sleeve being slidable within said housing when said plunger is depressed or retracted while said cavity is in an open position.

33. A device as claimed in claim 31 wherein said extracting surface is a zone extending longitudinally within said tubular member near said open end, said extracting surface being an extracting phase coating on an interior surface of said tubular member.

34. A device as claimed in claim 31 wherein the cavity is adjustable between an open position and a closed position.

35. A device as claimed in claim 34 wherein said closed end of said tubular member is connected to a plunger, said tubular member being slidable within said housing, said plunger being depressed when said cavity is in an open position to expose said tubular member outside of said cavity, said plunger being retracted before said cavity is moved to said closed position.

* * * * *